United States Patent [19]
Beaty et al.

[11] Patent Number: 5,909,285
[45] Date of Patent: Jun. 1, 1999

[54] THREE DIMENSIONAL INSPECTION SYSTEM

[76] Inventors: Elwin M. Beaty, 13529 Arthur St., Minnetonka, Minn. 55305; David P. Mork, 14605 34th Ave. North, No. 209, Plymouth, Minn. 55447

[21] Appl. No.: 08/955,198

[22] Filed: Oct. 21, 1997

Related U.S. Application Data

[63] Continuation-in-part of application No. 08/850,473, May 5, 1997.

[51] Int. Cl.[6] .............................. G01B 11/24; G06K 9/00
[52] U.S. Cl. ....................... 356/394; 356/237.1; 382/146; 348/126
[58] Field of Search .................................... 356/237, 394, 356/395, 396; 348/87, 126; 382/153, 291, 145, 146, 149, 150; 29/721, 759

[56] References Cited

U.S. PATENT DOCUMENTS

| | | |
|---|---|---|
| 4,638,471 | 1/1987 | van Rosmalen . |
| 4,825,394 | 4/1989 | Beamish et al. . |
| 4,886,958 | 12/1989 | Merryman et al. . |
| 4,943,722 | 7/1990 | Breton et al. . |
| 5,095,447 | 3/1992 | Manns et al. . |
| 5,113,581 | 5/1992 | Hidese ...................................... 29/840 |
| 5,133,601 | 7/1992 | Cohen et al. . |
| 5,140,643 | 8/1992 | Izumi et al. ................................ 382/8 |
| 5,173,796 | 12/1992 | Palm et al. . |
| 5,204,734 | 4/1993 | Cohen et al. . |
| 5,276,546 | 1/1994 | Palm et al. . |
| 5,307,149 | 4/1994 | Palm et al. . |
| 5,355,221 | 10/1994 | Cohen et al. . |
| 5,420,691 | 5/1995 | Kawaguchi .............................. 356/375 |
| 5,430,548 | 7/1995 | Hiroi et al. . |
| 5,452,080 | 9/1995 | Tomiya .................................... 356/237 |
| 5,563,702 | 10/1996 | Emery et al. . |
| 5,563,703 | 10/1996 | Lebeau et al. .......................... 356/237 |
| 5,574,668 | 11/1996 | Beaty . |

FOREIGN PATENT DOCUMENTS

WO9112489  8/1991  WIPO .
WO9207250  4/1992  WIPO .

*Primary Examiner*—Hoa Q. Pham
*Attorney, Agent, or Firm*—Han I. Sun; Emil Moffa

[57] ABSTRACT

A part inspection and calibration method for the inspection of integrated circuits includes a camera to image a precision pattern mask deposited on a transparent reticle. Small parts are placed on or above the transparent reticle to be inspected. A light source and overhead light reflective diffuser provide illumination. An overhead mirror or prism reflects a side view of the part under inspection to the camera. The scene of the part is triangulated and the dimensions of the system can thus be calibrated. A reference line is located on the transparent reticle to allow an image through the prism to the camera of the reference line between the side view and the bottom view. A precise reticle mask with dot patterns gives an additional set of information needed for calibration. By imaging more than one dot pattern the missing state values can be resolved using an iterative trigonometric solution. The system optics are designed to focus images for all perspectives without the need for an additional focusing element.

33 Claims, 14 Drawing Sheets

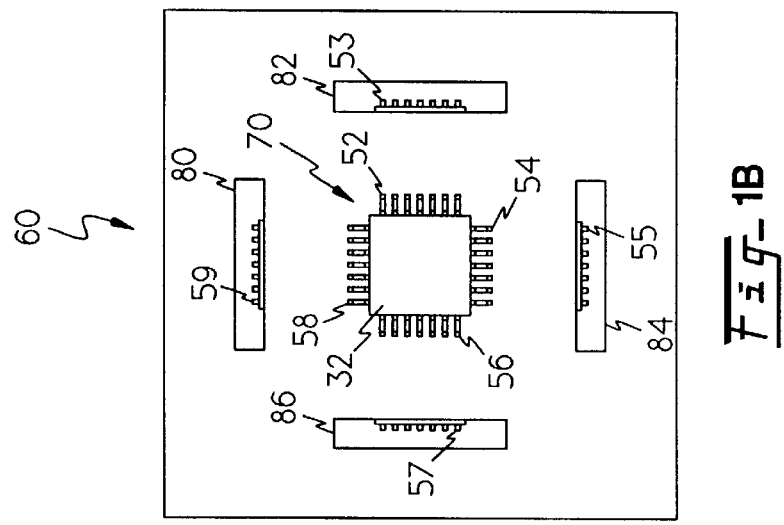
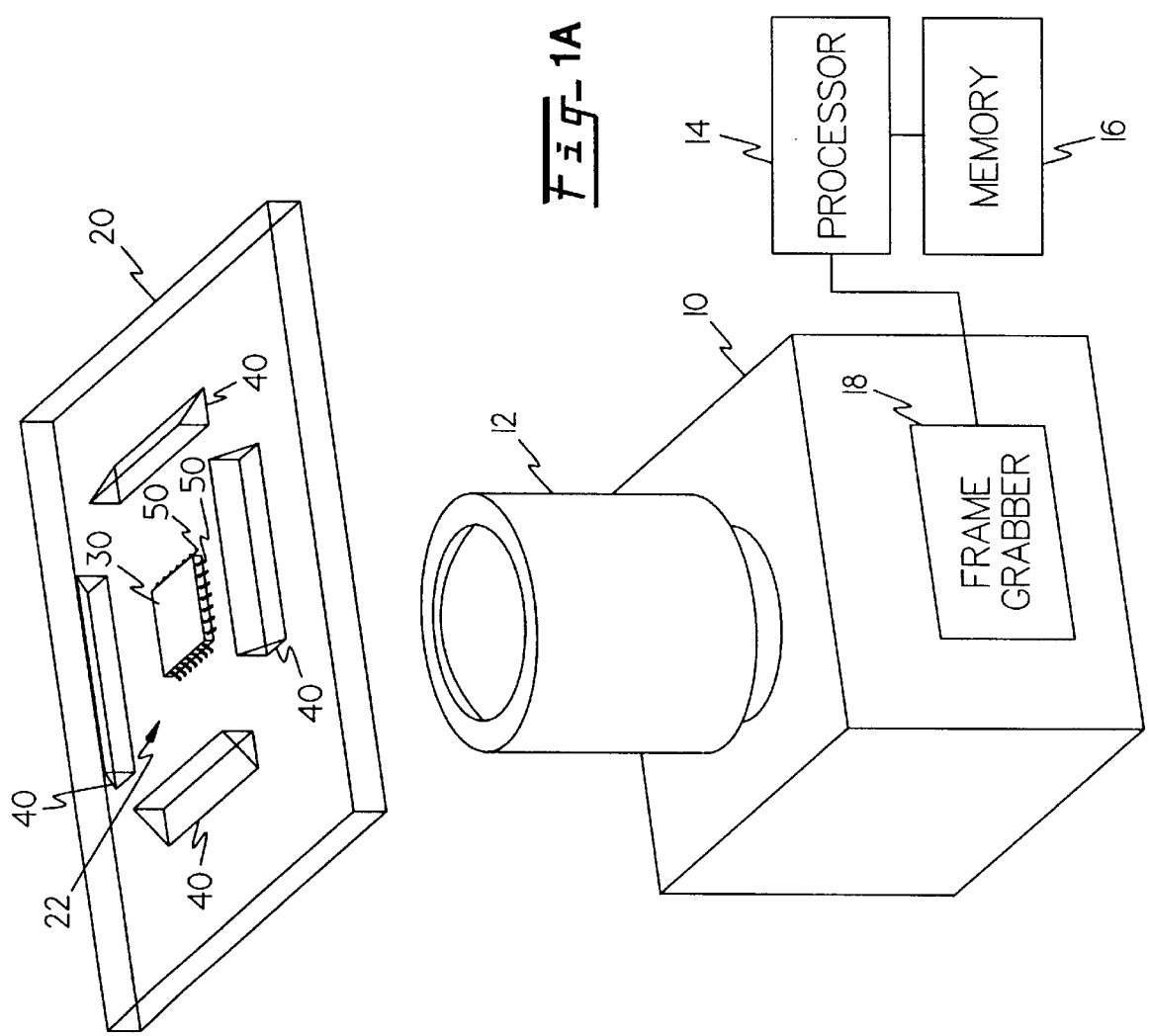

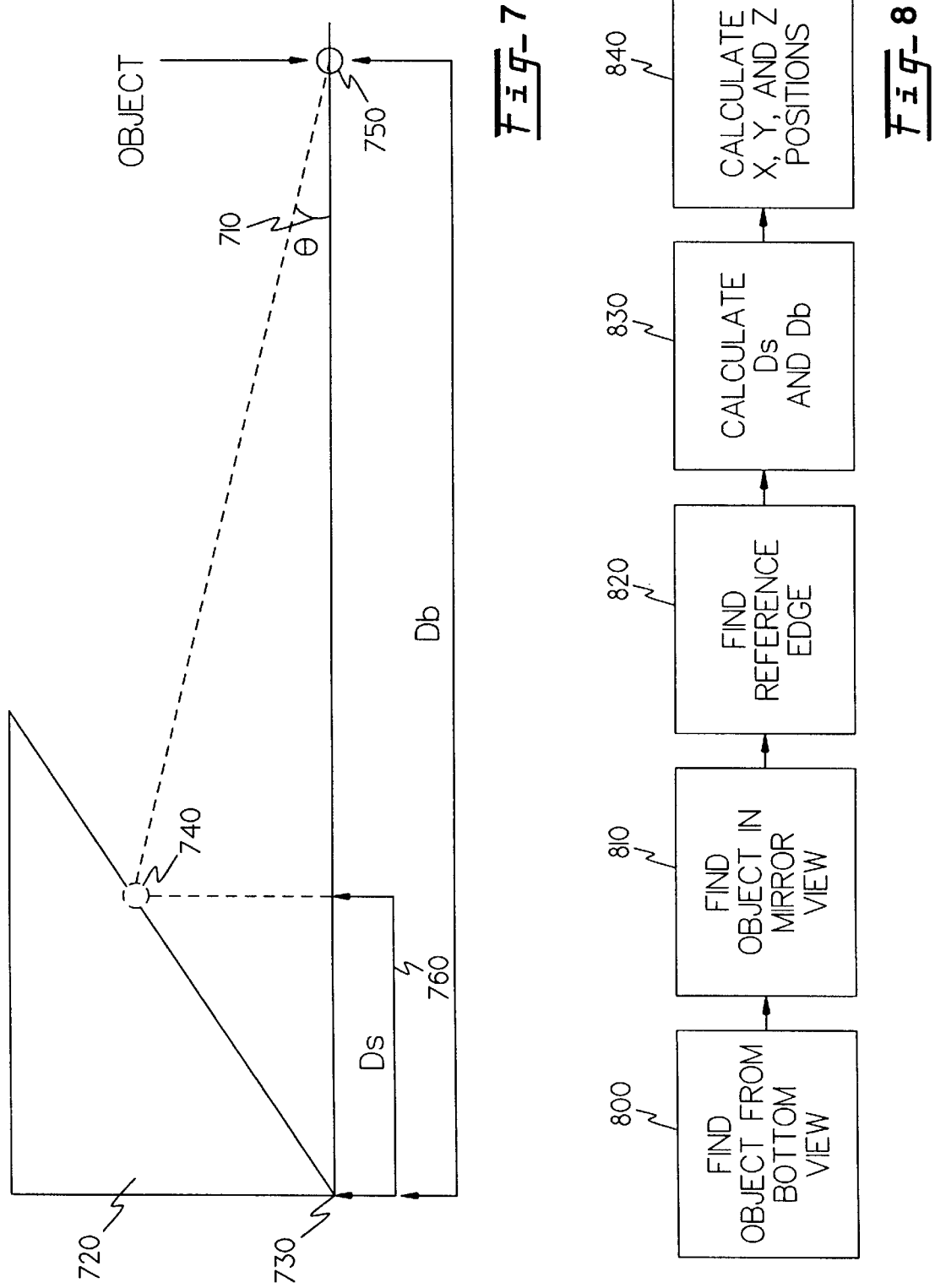

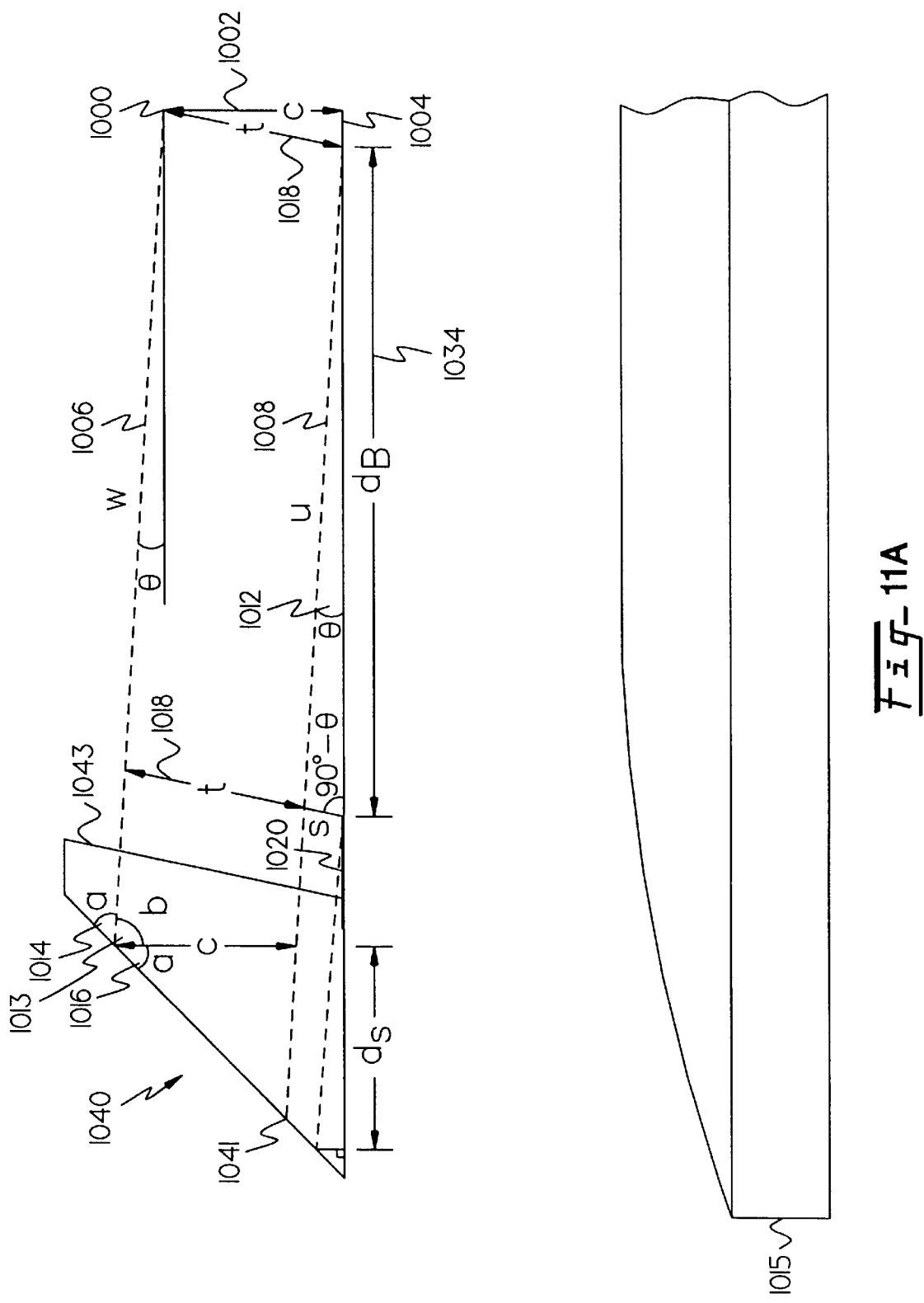

THREE DIMENSIONAL INSPECTION SYSTEM

CROSS-REFERENCE TO RELATED APPLICATION

This is a continuation-in-part of copending application Ser. No. 08/850,473 filed on May 5, 1997.

NOTICE RE COPYRIGHT

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

This invention relates to a method and apparatus for three dimensional inspection and, more particularly, a method and apparatus for three dimensional inspection of electrical component leads using a single axial camera, a single image, and a reference system.

BACKGROUND OF THE INVENTION

Prior art three dimensional inspection systems have involved multiple access mirrors and multiple cameras or a single camera and multiple images. These systems have been used to inspect integrated circuits and other small parts. The prior art requires a multiple number of images to accomplish the three dimensional inspections. Traditional prior art methods utilize a triangulation method that requires multiple images. Multiple images increase the cost of prior art solutions as well as the complexity and the time needed for inspection.

Prior art solutions do not include a method or apparatus for providing three dimensional inspections of a part having leads from a single image using a reference system, wherein the reference system comprises a reticle mask reference line, wherein the reference line is located between the bottom view and the side view of the part in a single image. Using a single image for three dimensional systems provides a speed and cost benefit. It is therefore a motivation of the invention to provide a three dimensional scanning system for a part having leads where the scanning system requires only one image of the part being taken with a reference line providing a view of the part through a prism or mirror.

Other scanning systems are disclosed in U.S. Pat. No. 5,173,796, issued Dec. 22, 1992 to Palm et al., entitled "THREE DIMENSIONAL SCANNING SYSTEM", U.S. Pat. No. 5,276,546, issued Jan. 4, 1994 to Palm et al., entitled "THREE DIMENSIONAL SCANNING SYSTEM", and U.S. patent application Ser. No. 08/850,473, filed May 5, 1997, entitled "THREE DIMENSIONAL INSPECTION SYSTEM" and the disclosures of which are incorporated herein, in their entirety, by the foregoing references thereto.

SUMMARY OF THE INVENTION

The invention provides a part inspection and calibration method and apparatus for the inspection of integrated circuits. The invention includes a camera to image a precision pattern mask deposited on a transparent reticle. Small parts are placed on or above the transparent reticle to be inspected. A light source and overhead light reflective diffuser provide illumination. An overhead mirror or prism reflects a side view of the part under inspection to the camera. The scene of the part is triangulated and the dimensions of the system can thus be calibrated. A reference line is located on the transparent reticle to allow an image through the prism to the camera showing the reference line between the side view and the bottom view. A precise reticle mask with dot patterns gives an additional set of information needed for calibration. The reference line and the reticle mask provide reference values. By imaging more than one dot pattern the missing state values can be resolved using a trigonometric solution. The system optics are designed to focus images for all perspectives without the need for an additional focusing element.

BRIEF DESCRIPTION OF THE DRAWINGS

To illustrate this invention, a preferred embodiment will be described herein with reference to the accompanying drawings.

FIG. 1A shows the apparatus of the invention for part inspection and calibration.

FIG. 1B shows an example image acquired by the system.

FIG. 7 shows a method for calibration of the optical elements.

FIG. 8 shows a flow chart of a method of the invention for determining three dimensional location.

FIGS. 11A, 11B, 11C, 11D, 11E and 11F show one embodiment of the invention to determine the position of a lead.

DETAILED DESCRIPTION OF THE PREFERRED EMBODIMENT

Figure 1C:
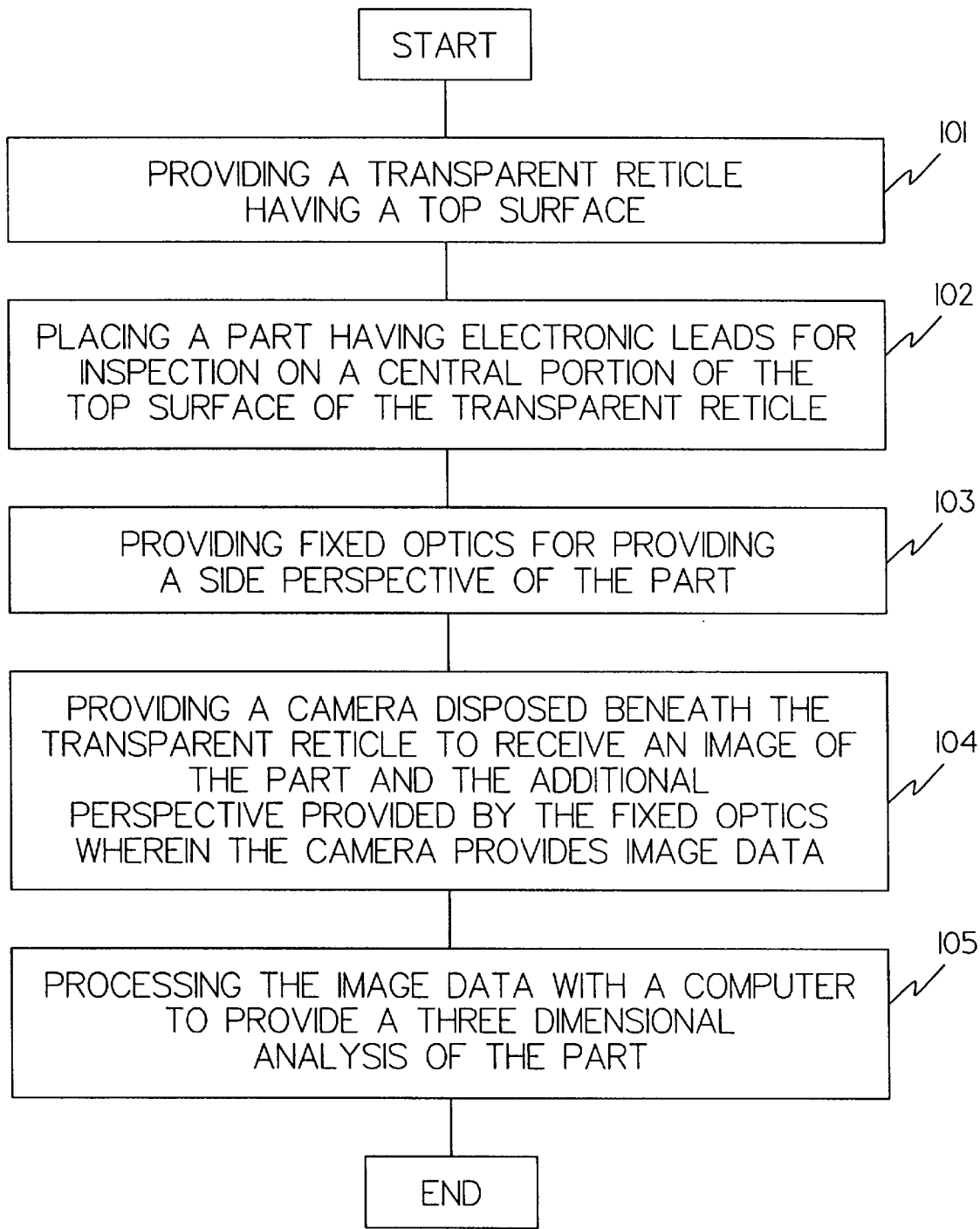
FIG. 1C shows a method for three dimensional inspection of electronic leads from a single image.

In one embodiment of the invention, the method and apparatus disclosed herein is a method and apparatus for three dimensional inspection of objects having electronic leads.

FIG. 1A shows the apparatus of the invention for three dimensional inspection. The apparatus includes a camera 10 with a lens 12 and a reticle 20. The reticle 20 includes a central region 22 for receiving a part 30 having a lead 50 for imaging by the camera. The camera 10 is located below the central region 22 of the reticle 20 to receive an image of the part 30. The reticle 20 includes optical elements 40 to provide additional perspectives of the part 30. The optical elements 40 are attached to the reticle and are located around the central region 22 to provide multiple side views of the part 30 to the camera 10. In one embodiment of the invention, the optical elements 40 may comprise prisms. In an alternate embodiment of the invention, the optical elements 40 may comprise mirrors.

The camera 10 is located to receive the image of part 30 and the additional perspectives provided by the optical elements 40. The camera 10 includes a frame grabber board 18 to capture the image. The optics of the camera 10 have a depth of focus encompassing the optical paths of the bottom view from the reticle 20 and the side views provided from the optical elements 40. The camera 10 provides an image data output to a processor 14 to perform a three dimensional inspection as described in conjunction with FIGS. 2A and 2B. The processor 14 may store the image in a memory 16.

FIG. 1B shows an example image acquired by the system shown in FIG. 1A. The image 60 obtained by the camera 10 includes a bottom view 70 obtained by the view through the reticle 20. The bottom view 70 shows an image of the part 32 and the leads 52, 54, 56, 58. The image 60 further includes four side views 80, 82, 84, 86 obtained by the view through reticle 20 and reflected off the optical elements 40. The side views 80, 82, 84, 86 show a respective side view of the part 32 and the corresponding leads 53, 55, 57, 59. For example, lead 53 in side view 82 corresponds to lead 52 in bottom view 70, lead 55 in side view 84 corresponds to lead 54 in bottom view 70, and so on. As will be appreciated by those skilled in the art, the invention will work with any number of side views. For example, one view may be used for inspecting a single row of leads. Two views may be used for two rows of leads.

Refer now to FIG. 1C which shows a method for three dimensional inspection of electronic leads from a single image. The method starts by providing a transparent reticle having a top surface in step 101. The method then places a part having electronic leads for inspection on a central portion of the top surface of the transparent reticle in step 102. The method then provides fixed optical elements for providing a side perspective of the part in step 103. The method then provides a camera located beneath the transparent reticle to receive an image of the part and the additional perspective provided by the fixed optical elements wherein the camera provides image data in step 104. The method then processes the image data with a computer to provide a three dimensional analysis of the part in step 105.

Figure 2A:
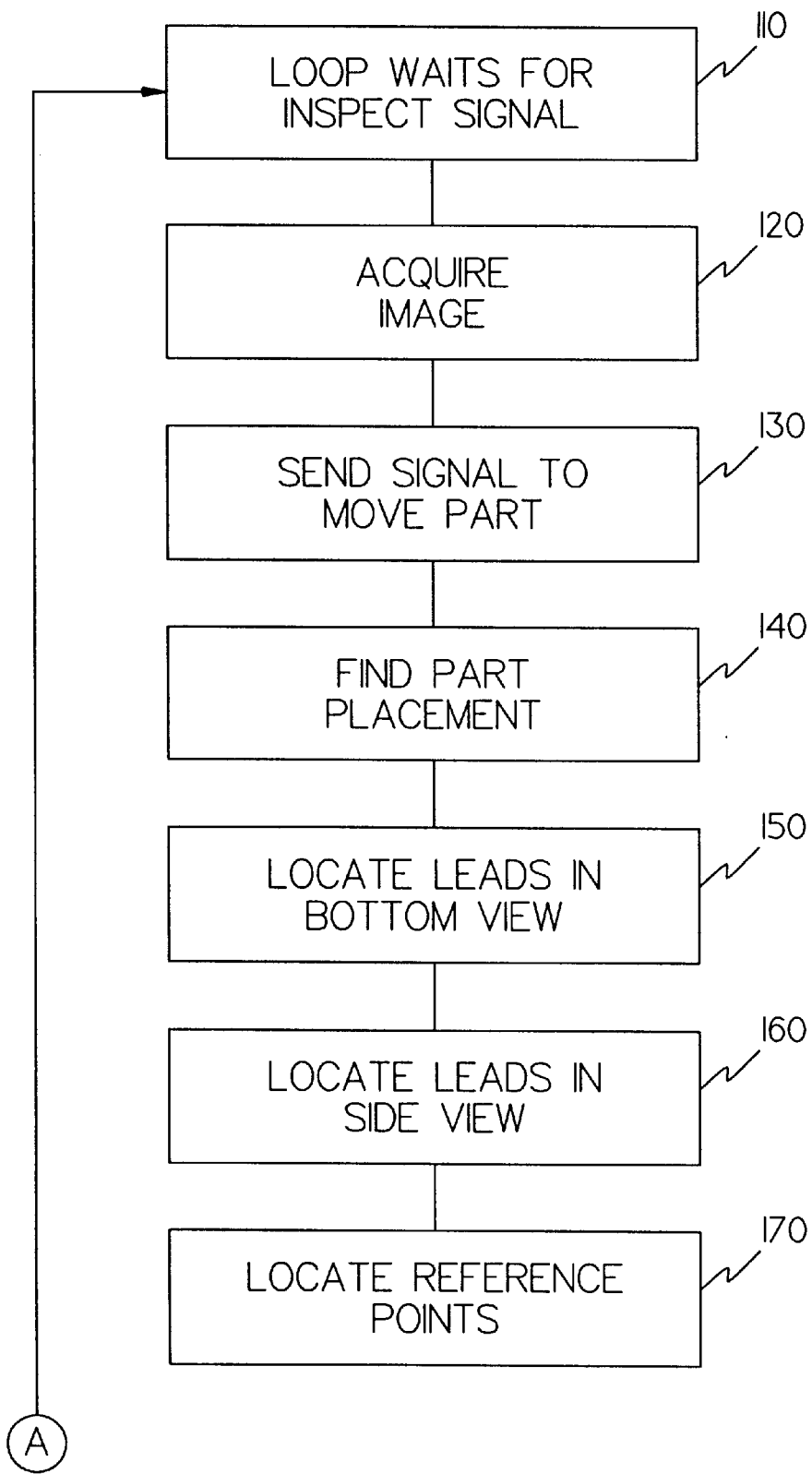
FIGS. 2A and 2B show a flow diagram of the three dimensional inspection loop of the invention.
Figure 2B:
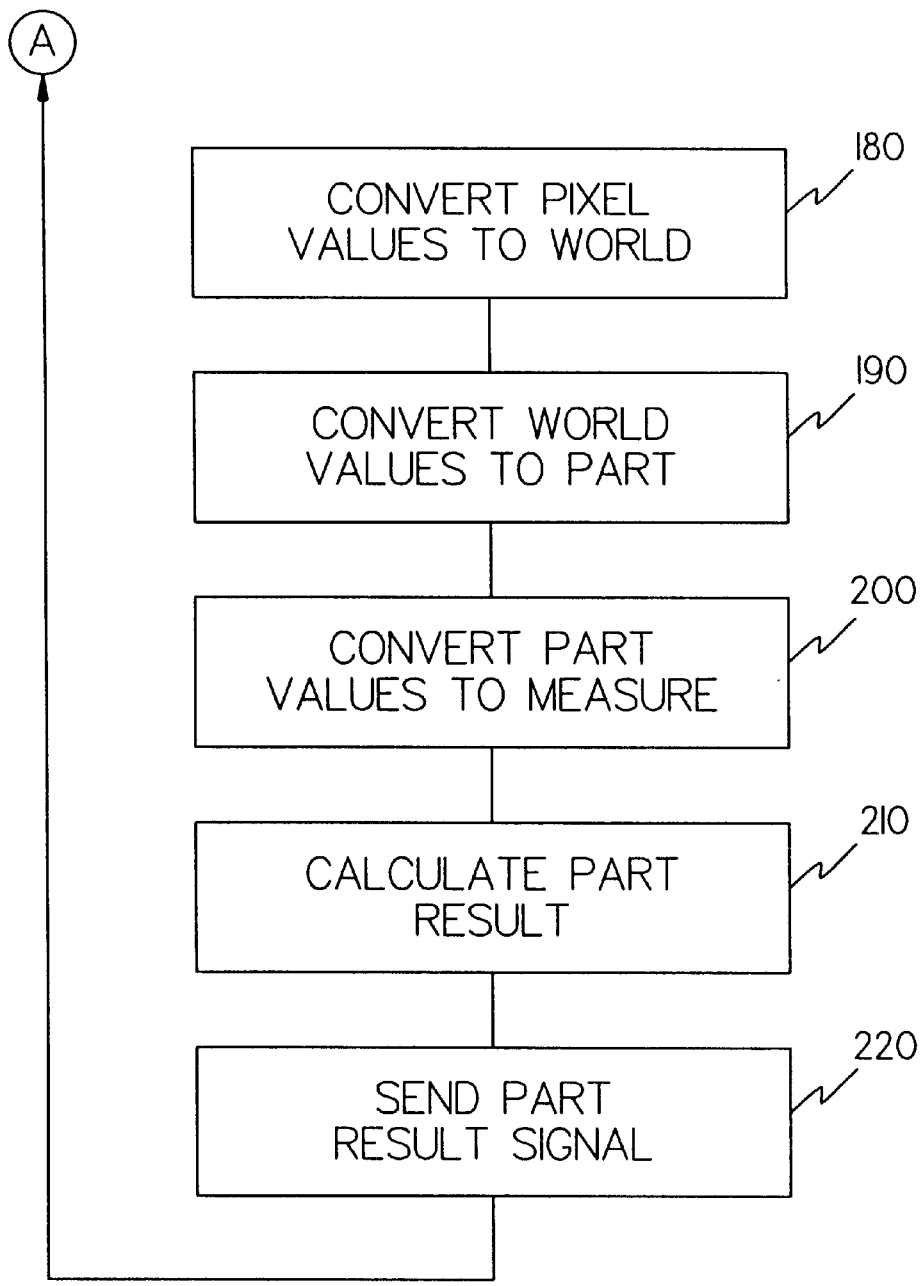

FIGS. 2A and 2B show a flow diagram of the three dimensional inspection loop of the invention. The process begins in step 110 by waiting for an inspection signal. When the signal changes state, the system initiates the inspection. The processor sends a command to a frame grabber board 18 to acquire an image of a part having leads from the camera in step 110. In step 120, the camera 10 captures an image comprising pixel values and the processor stores the image in memory. The image comprises information from both a bottom view of the part and a number of side views as shown in FIG. 1B.

Figure 9A:
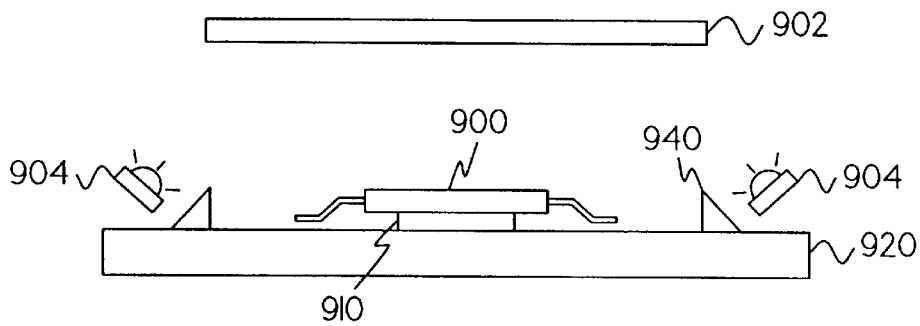
FIGS. 9A, 9B, 9C and 9D show alternate embodiments of the part holder and optical elements of the invention.
Figure 9B:
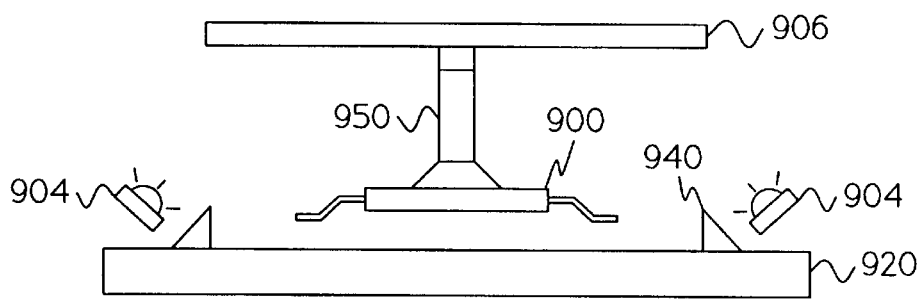
Figure 9C:
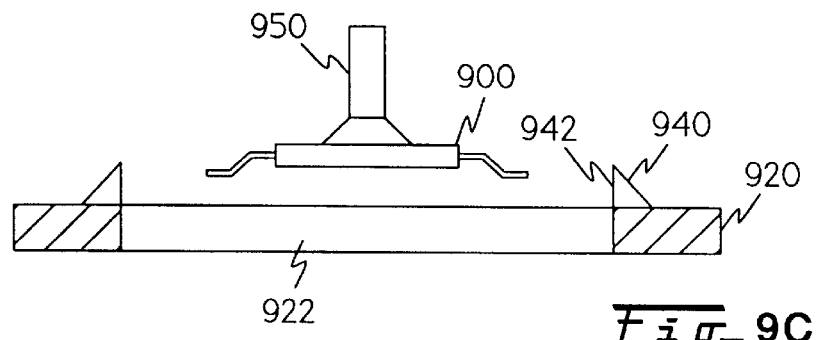
Figure 9D:
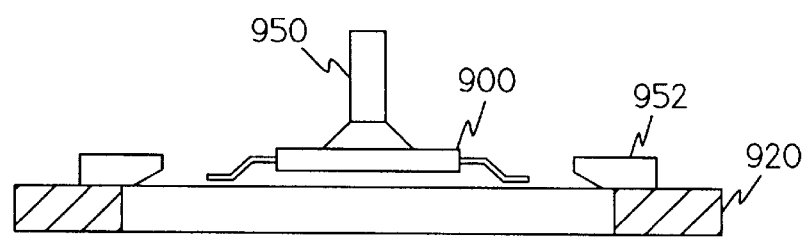

In step 130, the inspection system sends a signal to a part handler shown in FIGS. 9B, 9C and 9D that the part may be moved off the inspection reticle and that the next part may be put into place. The handler may proceed with part placement while the inspection system processes the stored image data.

Figure 4:
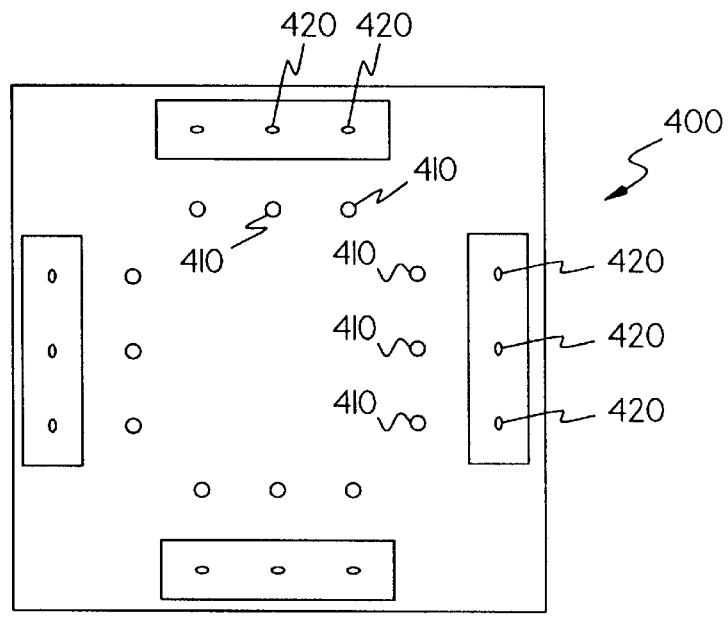
FIG. 4 shows one embodiment of a calibration dot pattern as viewed by a camera with four side optical elements.

The inspection system processes the pixel values of the stored image in step 140 to find a rotation, X placement, and Y placement of the part relative to a center point found during calibration of the inspection system using the reticle mask shown in FIG. 4. The processor determines these placement values finding points on four sides of the body of the part. In step 150, the processor employs a part definition file that contains measurement values for an ideal part. By using the measurement values from the part definition file and the placement values determined in step 140, the processor calculates an expected position for each lead of the part for the bottom view portion of the image. The processor employs a search procedure on the image data to locate the position of the lead closest to the expected position in the bottom view. The processor then determines the lead's X and Y position in pixel values by finding edges on three sides of each lead with a sub-pixel image processing method as shown in FIGS. 10A–10D.

Figure 6:
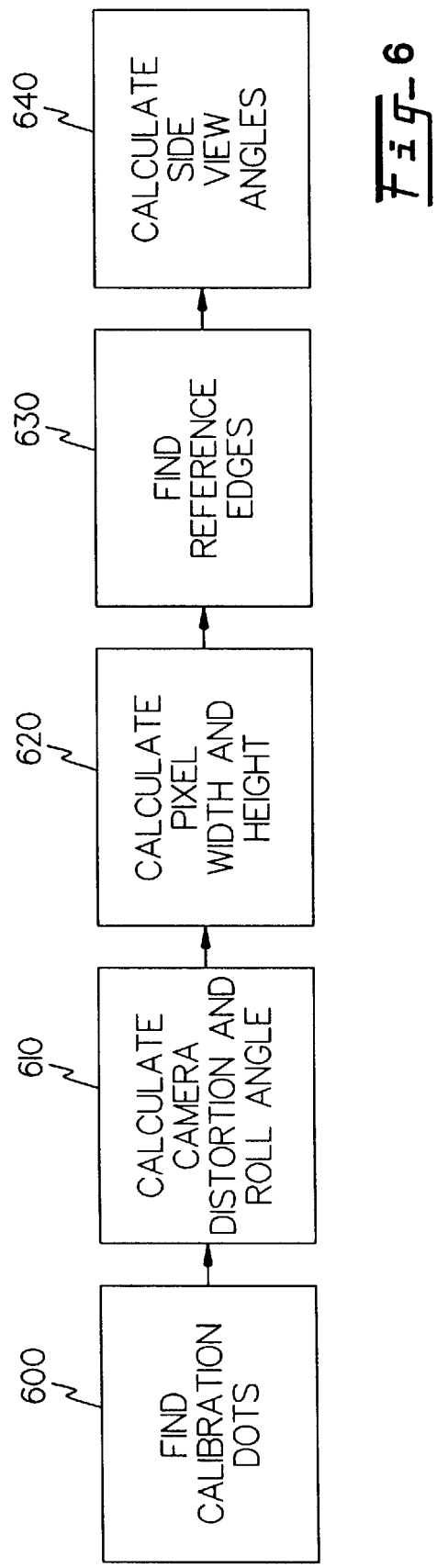
FIG. 6 shows a flow chart of a method of the invention used for system calibration.

The processor proceeds in step 160 to calculate an expected position of each lead in the side view of the image using the known position of the side view as determined during a calibration procedure as described in FIG. 6, and the position of the lead found in the bottom view. The processor employs a sub-pixel procedure to determine the Z position of the lead in pixel values as described in greater detail in conjunction with FIG. 3A.

After the processor locates the leads, the inspection loop flows to step 170 to determine a reference edge for each lead. The processor determines a closest reference edge for each lead found in the side view. In one embodiment, the juncture of the optical elements with the reticle may serve as a reference edge. In an alternate embodiment, a reference edge may be located on the transparent reticle. In another alternate embodiment, a virtual line of pixels may define the reference edge. The processor converts pixel values to world locations for each lead in step 180 by using the pixel values and parameters determined during calibration. The world locations represent physical locations of the leads in relation to the reference edge. The processor measures $D_S$ and $D_B$ dimensions and computes the Z dimension for each lead as further described in FIGS. 3A and 3B.

The processor then converts the world values to part values using the calculated part rotation, X placement, and Y placement in step 190 to define coordinates for the ideal part. The part values represent physical dimensions of the leads, such as lead length and lead width.

In step 200, these part values are compared to the ideal part values defined in the part file to calculate the deviation of each lead in three dimensions from the ideal location. In one example embodiment of the invention, the deviation values may include: tip offset, skew, bent lead, width and coplanarity. The processor compares these deviation values to predetermined thresholds with respect to the ideal part as defined in the part file in step 210 to provide an electronic lead inspection result. In one embodiment, the predetermined tolerance values include pass tolerance values and fail tolerance values from industry standards. If the measurement values are less than or equal to the pass tolerance values, the processor assigns a pass result for the part. If the measurement values exceed the fail tolerance values, the processor assigns a fail result for the part. If the measurement values are greater than the pass tolerance, but less than or equal to the fail tolerance, the processor designates the part to be reworked. The processor reports the inspection result for the part in step 220, completing part inspection. The process then returns to step 110 to await the next inspection signal.

Figure 3A:
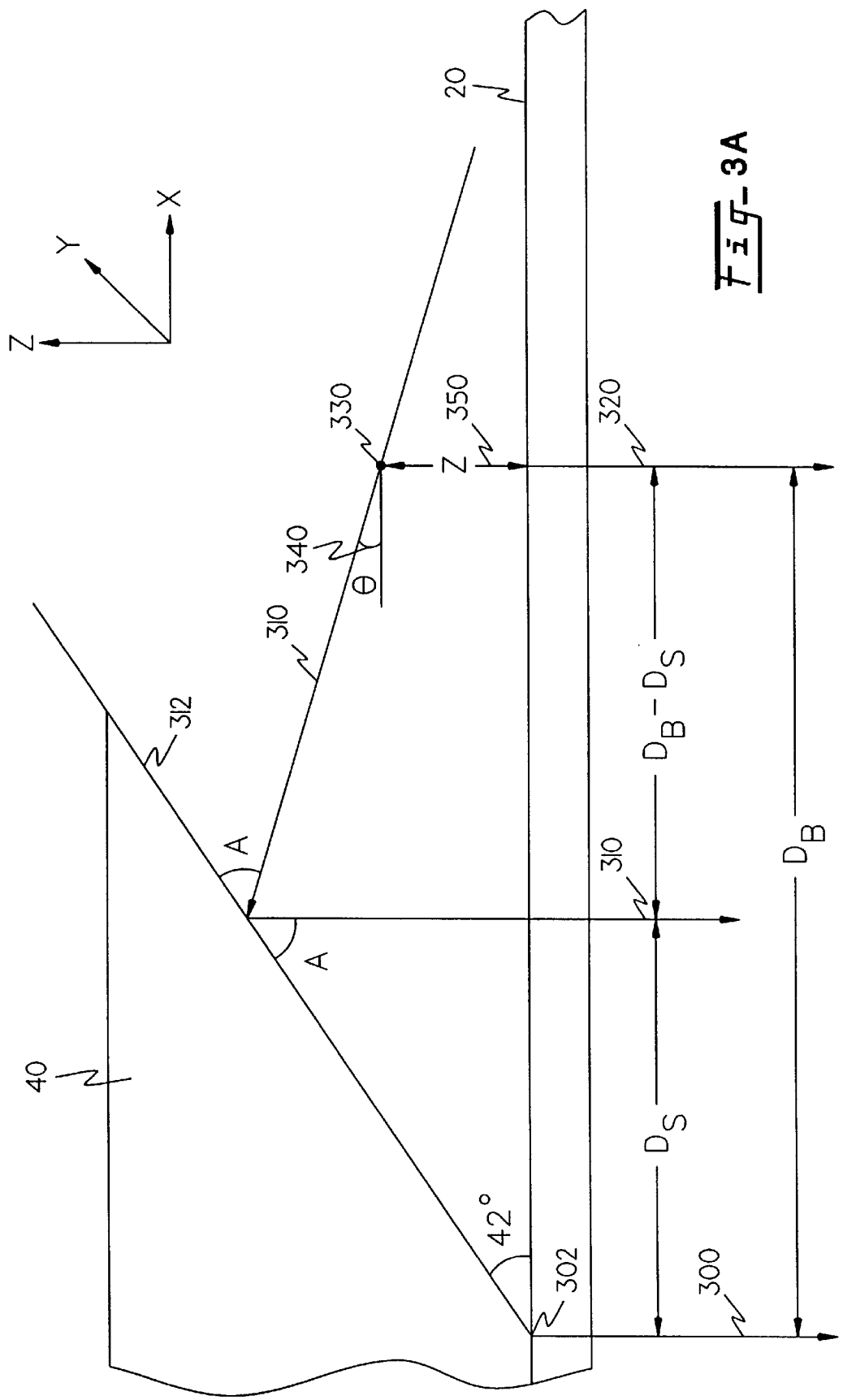
FIG. 3A shows one method of the invention used to locate an object in three dimensions.

FIG. 3A shows one method of the invention used to provide a three dimensional location of an object. Using parameters determined from the calibration procedure as shown in FIG. 6 and a single image, the processor computes a three dimensional location. The processor locates a reference line on the plane of the reticle 20 formed by the juncture of the optical element 40 with the plane of the reticle 20. Ray 300 shows the optical path from reference edge 302 to the camera 10. Rays 300, 310 and 320 are parallel with an axis of the camera 10. The processor measures a distance $D_S$ as the distance between the reference edge 302 and the reflected view of the object 330 of the reflective face 312 of the optical element 40 as shown by optical path 310. In one example embodiment, the angle of the reflective face 312 and the reticle 20 is 42°. One skilled in the art will realize that any angle may be used that will provide a view of the leads to the camera 10. The processor determines the distance $D_B$ as the distance between the reference edge 302 and the view of the object 330 as indicated by the optical path 320. Using the angle θ 340 defined by optical path 310 and a plane parallel to the reticle plane intersecting object 330, the processor determines the distance Z 350 of the object 330 above the reticle plane. FIG. 7 shows an example calculation of θ during a calibration of the system. The processor calculates the Z dimension using the equation:

$$Z = D_S \tan(45° - \theta/2) - (D_B - D_S) \tan \theta$$

where:

$D_S$=distance from the reference edge to the side view of the object;

$D_B$=distance from the reference edge to the bottom view of the object;

θ=angle formed by the ray emanating from the object reflected by the optical element and received by the camera and the plane intersecting the object parallel to the reticle plane; and Z=distance along the Z axis from the reticle plane to the object.

Figure 3B:
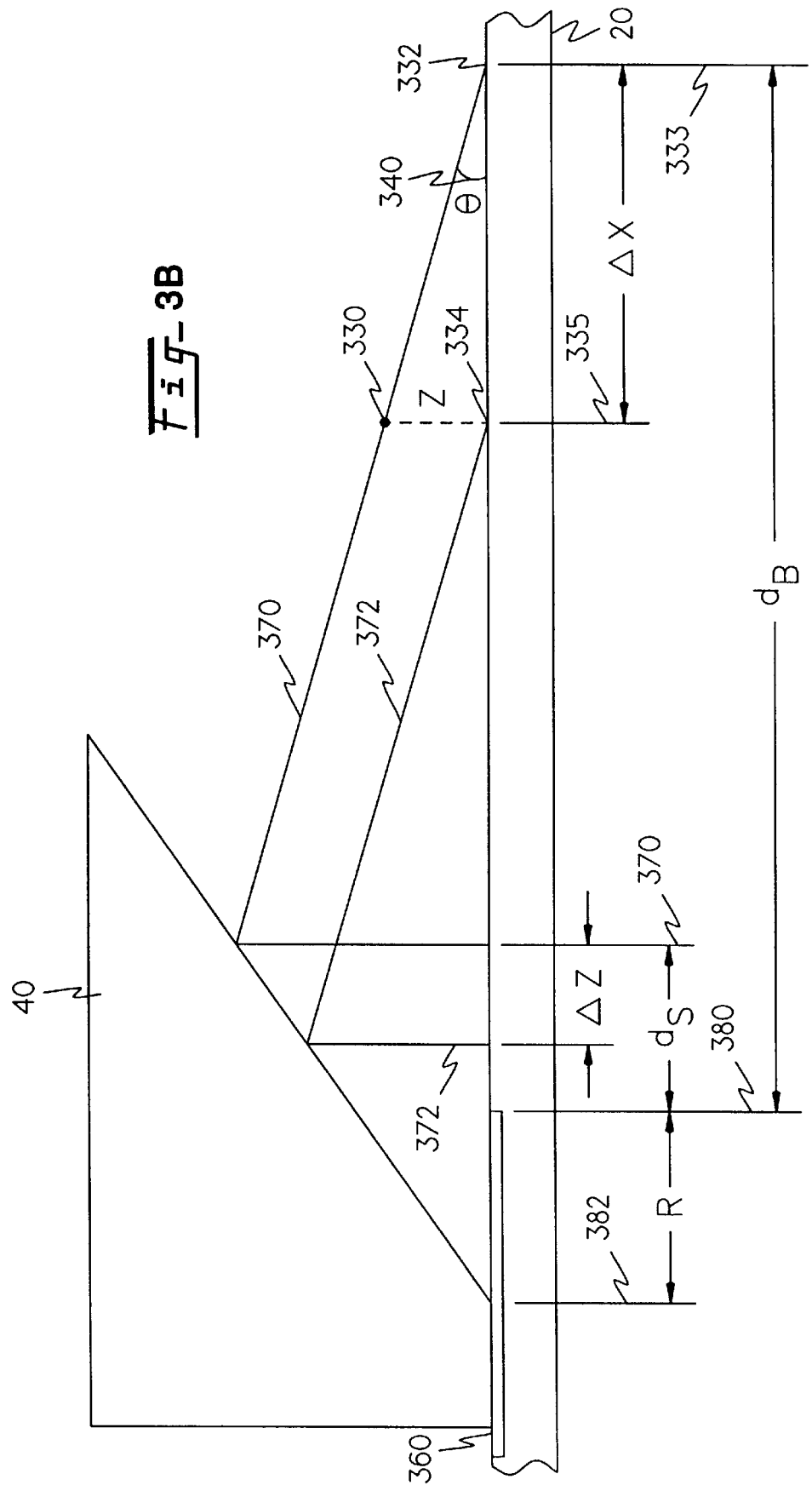
FIG. 3B shows an alternate method of the invention used to locate an object in three dimensions.

FIG. 3B shows an alternate method of the invention used to locate an object in three dimensions. In this method, the processor 14 begins by locating a reference line 360 located on the reticle 20. In one embodiment, an attachment of the optical element 40 with the reticle 20 may provide the reference line 360.

The processor 14 determines an angle θ 340 that is dependent upon the angle of the face 312 of the optical element 40 to the plane of the reticle 20. The angle θ 340 is determined by using two points 332 and 334. The processor 14 determines a distance between points 332 and 334 by measuring the distance between two rays 333 and 335 that are parallel to the axis of the camera and extending downward from points 332 and 334. The processor then examines the side view for the corresponding rays 370 and 372 received by the camera from the optical element 40. The distance between these two rays 370 and 372 in the side view is measured as ΔZ. θ is determined using the following equation:

$$\theta = \text{ARCTAN}\left(\frac{\Delta Z}{\Delta X}\right).$$

The process then determines an offset R where R is a measure of a distance from the intersection 382 of the face 312 of the optical element and the plane of the reticle 20 and the edge of the reference line 360. The offset R is determined according to the following equation:

$$R = \frac{(d_B - d_s)\tan\theta}{\tan(45° - \theta/2)} - d_s$$

where: $d_S$=distance from a reference edge to the side view image of the object, which is the distance from rays 380 and 370;

$d_B$=distance from a reference edge to the bottom view image of the object, which is the distance between rays 380 and 333;

θ=angle formed by the ray emanating from the object reflected by the fixed optical element and received by the camera and the plane intersecting the object parallel to the reticle plane; and R=offset of reference line 360 and the intersection 382 between a reflective face of the optical element 40 and the transparent reticle 20.

The processor then determines the height Z of an object above the upper surface of the reticle 20, using the following equation:

$$Z = (d_S + R) \tan(45° - \theta/2) - (d_B - d_S) \tan \theta.$$

where Z equals the distance along the Z axis from the reticle plane to the object.

Figure 5:
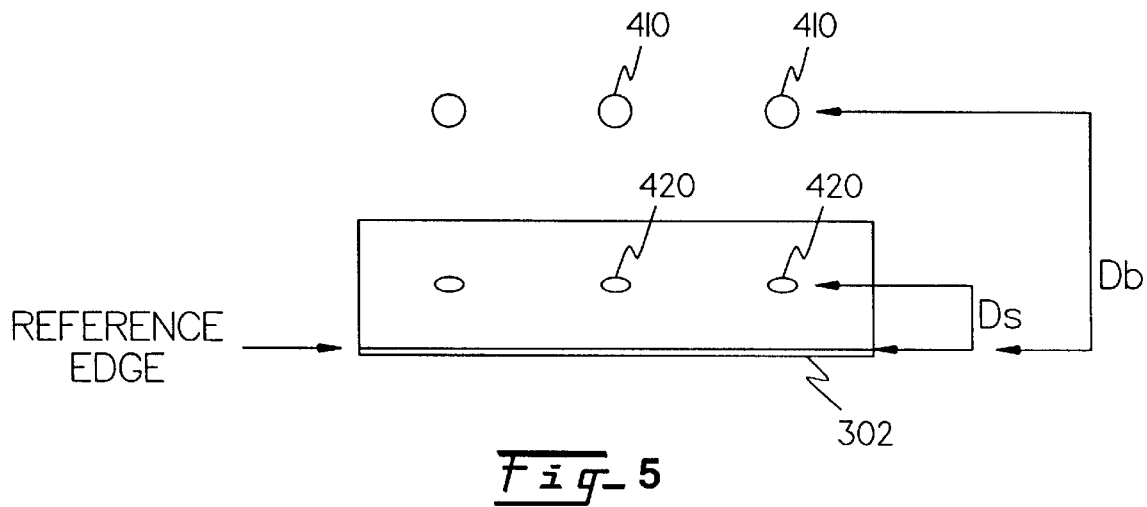
FIG. 5 shows a method of the invention for determination of $D_S$ and $D_B$.

In one embodiment of the invention, the system is calibrated by placing a pattern of calibration dots of known spacing and size on the reticle plane. FIG. 4 shows one embodiment of a calibration dot pattern as viewed by the camera 10 with four side optical elements, fewer or more side optical elements may also be used. The camera receives an image including a bottom view and four side views from the optical elements located on the reticle plane. The calibration dots appear as direct images 410 and reflected images 420. FIG. 5 shows the relationship between the direct image 410, the reflected image 420 and the reference edge 302 and the values of $D_S$ and $D_B$.

FIG. 6 shows a method of the invention used to calibrate the system using the reticle mask 400. The method begins at step 600 by finding the calibration dots. The processor finds a location and size of each dot visible directly from the bottom view and stores these results in memory. By comparing these results to known values stored in memory, the processor calculates the missing state values for the bottom calibration in steps 610 and 620. For example, in step 610 the processor determines camera distortion and roll angle and in step 620 the processor measures pixel width and height. These state values include pixel width and pixel height, pixel aspect ratio, optics distortion, and camera orientation with respect to the dot pattern. The processor then stores these results in memory. These results provide conversion factors for use during analysis to convert pixel values to world values.

The process flows to step 630 where the processor finds calibration dots visible in side views and reference edges. From these values, the processor determines the side view angles of the optical elements 40 in step 640 as shown in FIG. 7. The processor begins by finding the missing state values for each side mirror calibration from the data. These include the position of the mirror to the reticle plane. The state values are stored in memory.

FIG. 7 shows how the system determines angle θ 710 for the optical element 720 using $D_S$ and $D_B$. The system locates a reference edge 730 and uses a reflected image 740 of the object 750 to determine a distance $D_S$ 760. $D_B$ is determined by the distance from the reference edge 730 and the object 750. The angle calculation for angle θ 710 may be determined by the following calculation:

$$\theta = \text{ArcSin}\left[\frac{D_S}{D_B}\right].$$

where $D_S$=distance from a reference edge to the side view image of the object, which is the distance from rays 380 and 370;

$D_B$=distance from a reference edge to the bottom view image of the object, whcih is the distance between rays 380 and 333; and θ=angle formed by the ray emanating from the object reflected by the fixed optical element and received by the camera and the plane intersecting the object parallel to the reticle plane.

Once angle θ is known, the inspection system may use these known values to determine the three dimensional location of an object in space.

FIG. 8 shows one embodiment of a method of the inspection system of the invention to determine a three dimensional position of an object in space. The method begins in step 800 by finding an object from the bottom view. Using a search method, the processor determines coordinates for the object. In one embodiment, the processor may employ a subpixel method as shown below in FIGS. 10A–10D to find a repeatable position. The method then proceeds to step 810 to find the object in a side view. The processor determines a subpixel location for the object in the same manner as for the bottom view. The processor finds a reference edge to a subpixel location in step 820, and then computes the observed values for $D_S$ and $D_B$ in step 830. From these known values, the processor may determine the x, y and z positions of the object in step 840.

FIGS. 9A, 9B, 9C and 9D show alternate embodiments of the part holder, optical elements and illumination elements of the invention. In FIG. 9A, a pedestal 910 is attached to the central portion of the reticle 920. A part 900 may be received on the pedestal 910 for analysis. Light sources 904 provide illumination. An overhead light reflective diffuser 902 is fixed above the reticle 920 and is positioned to receive illumination from the light sources 904 and provides diffused illumination for backlighting for the bottom view of part 900. In one preferred embodiment, the light sources 904 comprise light arrays mounted on four sides of the reticle 920 to provide even illumination for each view.

In FIG. 9B, a vacuum holder 950 is used to suspend a part 900 above the top surface of the reticle 920. The vacuum holder 950 suspends the part 900 substantially parallel to the face of the reticle 920. An overhead light reflective diffuser 906 may be mounted on the vacuum holder 950 to receive light from the light sources 904. FIG. 9C shows a vacuum holder 950 suspending a part 900 above a reticle 920 where a central portion 922 of the reticle has been cut out. The central portion 922 of the reticle 920 has been cut out so that an inward face 942 of a prism 940 is substantially in line with the cut out portion of the reticle 920. FIG. 9D shows a configuration similar to that shown in FIG. 9C, except that a mirror 952 is used in place of the prism 940.

Figure 10A:
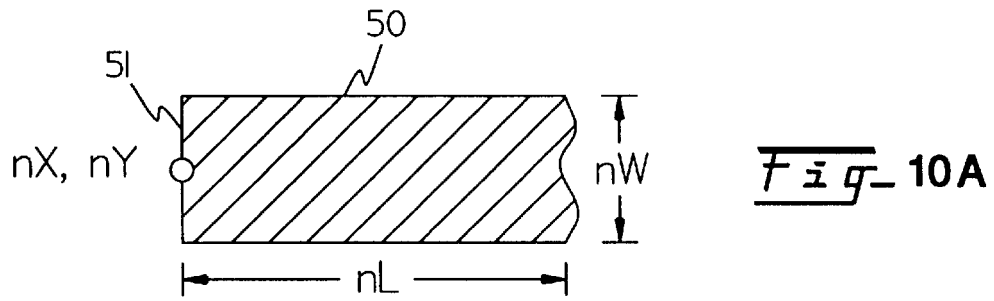
FIGS. 10A, 10B, 10C and 10D show one embodiment of the subpixel lead dimension measurement method.

Refer now to FIGS. 10A–10D which show one embodiment of the subpixel lead dimension measurement method. The processor begins with known parameters determined from the bottom view to find an ideal location center for a lead 50 having a lead tip 51. Depending on the size of a part and other parameters such as lighting conditions, the ideal location center of the lead tip 51 may vary. The processor defines a region of interest, 11×19 pixels for example, around the ideal location center, shown in FIG. 10A as the coordinates nX, nY. For example, the camera is a CCD camera that contains 1024×1024 pixels with a pixel representing approximately 1.6 thousandths of an inch of the lead. Other optical systems and camera types may be used without deviating from the spirit and scope of the invention. The size of the region of interest is chosen such that only one lead is contained in the region so that no other adjacent lead is contained in that region of interest. Using nW, an expected width in pixels, and nL, an expected length available of the lead 50 up to the body of the part, an expected lead dimensions are found as shown in FIG. 10A. Within the region of interest, a processor finds a lead tip 51 by moving from the outside edge opposite the lead tip 51 toward the lead tip 51 one pixel at a time. The processor determines the pixel having the maximum gradient to be the edge of the lead tip dT. The gradient for each pixel is found by subtracting a gray scale value of the pixel from the gray scale value of the next pixel. To reduce the possible effects of noise, the processor may proceed by averaging groups of three or more pixels, as an example, rather than using individual pixels. When the lead tip 51 is found, the processor determines the two lead tip edges' positions, $dS_1$ and $dS_2$ by moving five pixels, for example, into the lead along an axis parallel to the lead as defined by the ideal part. Then the method moves toward each of the side edges along a line perpendicular to the lead until a maximum gradient is found along the line. The pixel with the maximum gradient $dS_1$ and $dS_2$ are defined as the side positions.

Figure 10B:
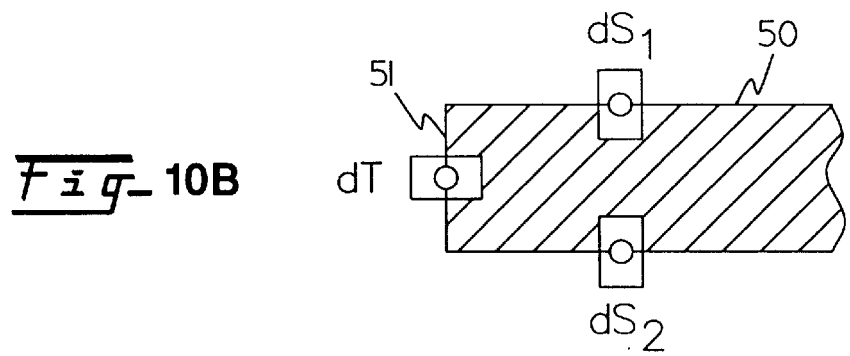

The processor then performs a subpixel operation as shown in FIG. 10B to find a more accurate seed position for a second subpixel operation. The processor defines a small 3×5 box around each position dT, $dS_1$ and $dS_2$. The subpixel operation begins on dT by averaging the three pixels in each column moving left to right and finding a more repeatable seed position dT. Likewise, more accurate seed positions $dS_1$ and $dS_2$ are found for the side locations moving from the non-lead edge into the lead while averaging the pixels in each row.

Figure 10C:
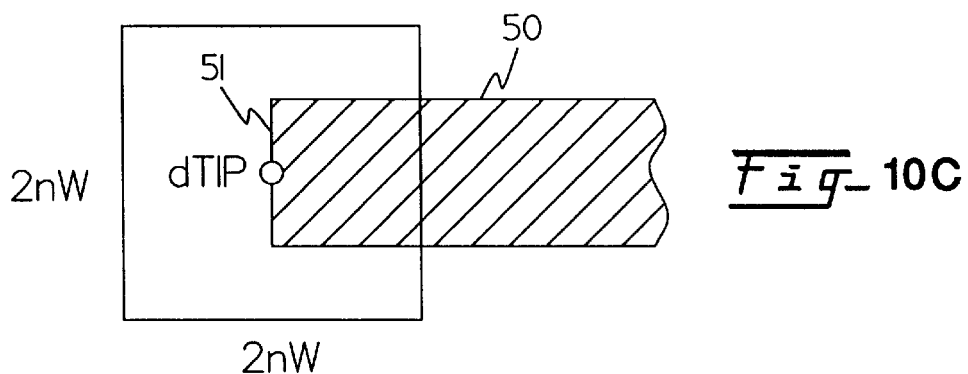

Once these new seed pixels have been determined, the processor determines tip position using the new seed point dTip and defining a large subpixel box of size 2 nW×2nW where the tip point is centered left to right on dT, and centered top to bottom on $(dS_1$ and $dS_2)/2$ as shown in FIG. 10C. Once again, the processor moves from left to right from a non-lead edge into the lead while averaging the pixels in each column to find dTip as the tip position. By using a larger box having more pixels, a more repeatable result is obtained.

Figure 10D:
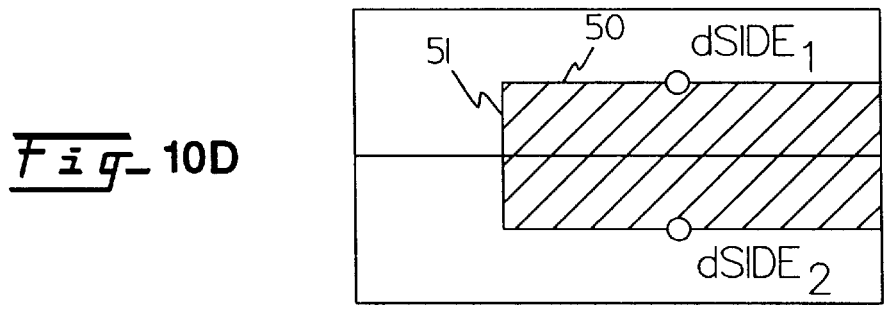

Likewise, as shown in FIG. 10D, the side positions are found using the seed positions $dS_1$ and $dS_2$ with a subpixel box of dimensions nL×nW. For one box the seed position is $dS_1$ and (dTip+nL/3). For the second box the seed position is $dS_2$ and (dTip+nL/3). The processor moves towards the lead averaging the pixels in each row, and using the subpixel process shown below, determines a subpixel location of the lead edges as $dSide_1$ and $dSide_2$. The width of the lead is then computed as $dSide_1-dSide_2$.

One example of subpixel edge detection implemented in the C language is shown below.

```
void IML__FindHorzEdge(int nXseed,int nYseed,
                int nWidth,int nLength,
                double * dEdge)
{
    int nXstart = nXseed − (nLength − 1) /2;
    int nYstart = nYseed − (nWidth − 1) /2;
    int nXstop = nXstart + nLength;
    int nYstop = nYstart + nWidth;
```

-continued

```
int *nArray[MAX_LENGTH];
double d1, d2, d3;
double dL = nLength;
double dM1 = 0.0;
double dM2 = 0.0;
double dM3 = 0.0;
double dM11;
for (int x=nXstart;x<nXstop;x++)
{
    d1 = 0.0;
    nArray[x-nXstart] = 0;
    for (int y=nYstart;y<nYstop;y++)
    {
        nArray[x-nXstart] += GET_PIXEL(x,y);
    }
    d1 = nArray[x-nXstart];
    d2 = d1 + d1;
    d3 = d2 + d1;
    dM1 += d1;
    dM2 += d2;
    dM3 += d3;
}
dM1 /= dL;
dM2 /= dL;
dM3 /= dL;
dM11 = dM1 + dM1;
double dS1 = dM3 - dM1 * (3.0 *dM2-2.0*dM11);
double dS2 = (dM2 - dM11) * sqrt(fabs (dM2-dM11));
if (dS2 == 0.0) dS2 - 1.0;
double dS3 = dS1 / dS2;
double dP = 0.5-dS3/(2.0*sqrt(4.0 + dS3 * dS3));
double dE = dP*dL + 0.5;
if (nArray [0] > nArray[nLength - 1])
    *dEdge = (double)nXseed - (double) (nLength+1)/2.0 + dE;
else
    *dEdge = (double)nXseed + (double) (nLength+1)/2.0 - dE;
} © 1997 Scanner Technologies, Inc.
```

Refer now to FIGS. 11A–11E which show an embodiment of the invention. In one embodiment, an attachment of the optical element 1040, which may comprise a prism, with the reticle 1004 may provide the reference line 1020. However, the attachment, which may be made with glue, may not provide a precise line. In an alternate embodiment, the reference line 1020 is located on the reticle 1004 at the intersection of the transmissive face 1043 of the optical element 1040 and the reticle 1004. The width of the reference line 1020 is chosen to be sufficiently narrow so as not to obscure the view of the part 1000, which may comprise a lead tip of the lead of an electronic component, from the camera 1015 off the reflective surface 1041 of the optical element 1040. The width of the reference line 1020 may be selected to obscure the intersection of the transmissive face 1043 and the reticle 1004 and extend beyond the upper overhang of the optical element 1040. Imprecision may be introduced by an uneven line in the intersection of the transmissive face 1043 and the reticle 1004 caused by an adhesive used to attach the optical element 1040 to the reticle 1004. The width of the reference line allows for measurement without the imprecision introduced by the attachment of the optical element 1040 to the reticle 1004.

FIG. 11A shows an actual position of the part 1000 located a distance c 1002 which represents the distance above the plane of the reticle 1004 of the part 1000. The distance c 1002 represents the distance in the z dimension of the part 1000 above the plane of the reticle 1004. Ray w 1006 shows an optical path of a ray passing perpendicularly through the plane of the reticle 1004, reflecting off a back plane 1041 of the optical element 1040 and passing through the location of the part 1000. Ray u 1008 shows the optical path of a ray passing upward perpendicularly through plane of the reticle 1004 reflecting off the back plane 1041 of the prism 1040 and passing through the point directly below part 1000. Ray u 1008 is parallel to ray w 1006 and is separated by distance c from ray 1006 in the z dimension. The reflection of rays w 1006 and u 1008 off the back plane 1041 of the prism 1040 form an angle b 1013 and angles of incidence a 1014 and reflection a 1016. Angle θ 1012 is defined as the angle formed at the intersection of ray u 1008 and plane of the reticle 1004. The distance t 1018 is the distance from the part 1000 and the ray u 1008 where t 1018 is perpendicular to the ray u 1008. $d_B$ 1034 is the distance along the x or y dimension from the leading edge of the reference line 1020 and the z projection intersection of the part 1000 and the plane of the reticle 1004.

Figure 11B:
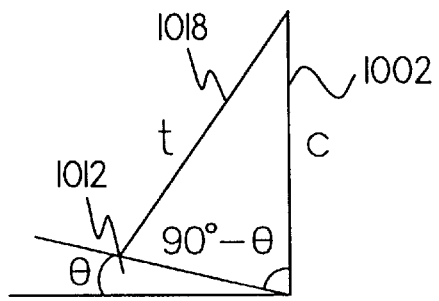

FIG. 11B shows a reduced illustration of the relationships between angle θ 1012, distance c 1002 and distance t 1018. The following equations illustrate the relationships between these values.

$$\sin(90 - \theta) = t/c$$

$$c = \frac{t}{\sin(90 - \theta)}$$

$$D = 45° - \theta/2$$

$$b = 90° - \theta$$

$$a = 45° + \frac{\theta}{2}$$

Figure 11C:
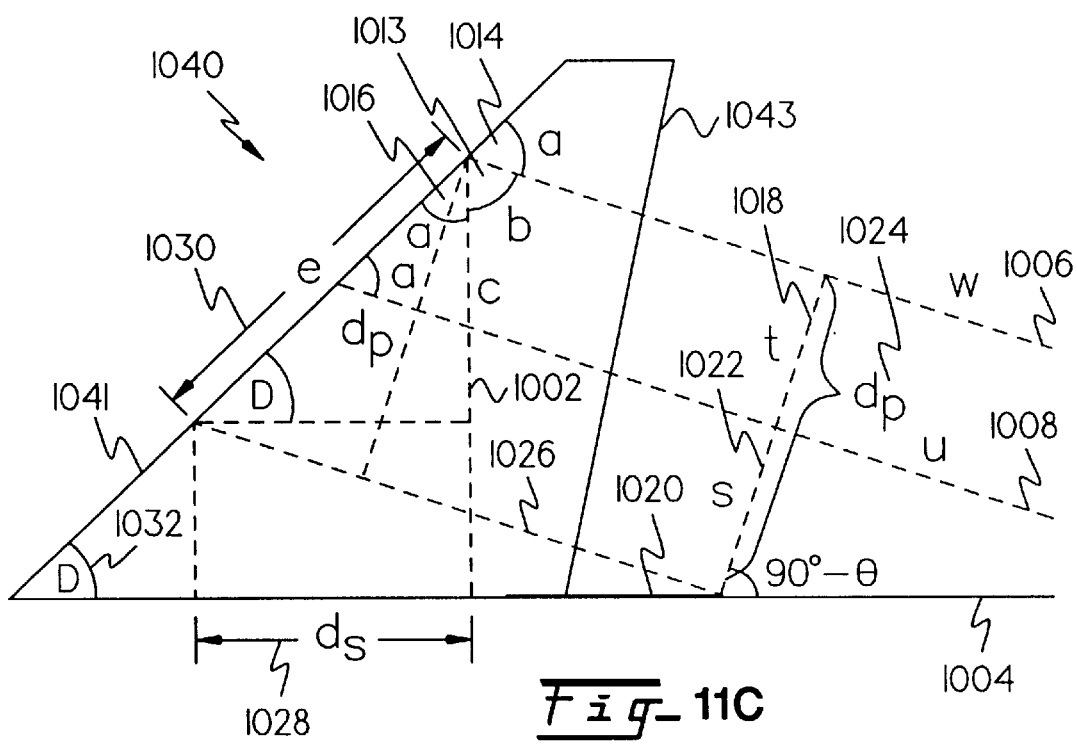

Refer to FIG. 11C which shows a detailed illustration of relationships formed by reference line 1020 and the location of the part 1000. The distance s is the distance from the leading edge of the reference line 1020 and the ray u 1008 along a path parallel to the distance t 1018. The distance dp 1024 is the sum of the two distances t 1018 and s 1022. Thus, $$dp=t+s$$

and $$t=dp-s.$$

Optical path 1026 is formed by the reflection of a ray passing perpendicular through the plane of the reticle 1004 reflecting off the back plane 1041 of the prism 1040 and passing through the leading edge of the reference line 1020. The distance ds 1028 is a measure of the distance in the plane of reticle 1004 of ray w 1006 from ray 1026 after reflection off the back plane 1041 of the prism 1040. The distance e 1030 is a measure of the distance of the points of intersection of the ray w 1006 from ray 1026 on the back plane 1041 of the prism 1040. The angle D 1032 is the angle of the back plane of the prism 1040 and the plane of the reticle 1004. Using these measures, the following relationship is determined.

$$\sin \theta = S/d_B$$

Figure 11D:
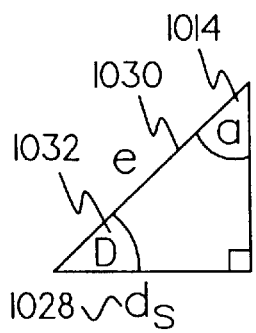

FIG. 11D reduces the relationships of e 1030, angle a 1014, angle d 1032 and ds 1028. Therefore, $$\frac{e}{\sin 90°} = \frac{ds}{\sin a} = \frac{ds}{\sin(90° - D)} = \frac{e}{1}$$

$$e = \frac{ds}{\sin(90° - D)}$$

Figure 11E:
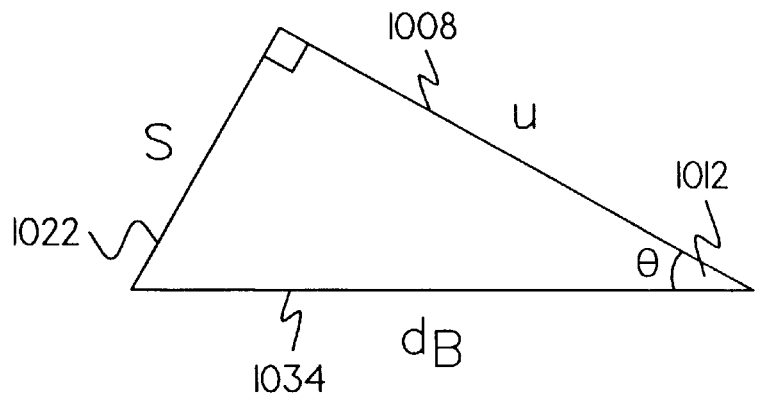

FIG. 11E shows the relationships of the distance s 1022, ray u 1008, angle θ 1012 and $d_B$ 1034.

$$\frac{d_B}{\sin 90°} = \frac{S}{\sin\theta} = \frac{u}{\sin(90°-\theta)} = \frac{d_B}{1}$$

$$d_B = \frac{S}{\sin\theta} = \frac{u}{\sin(90°-\theta)}$$

$$u = d_B[\sin(90°-\theta)]$$

$$S = d_B \sin\theta$$

Figure 11F:
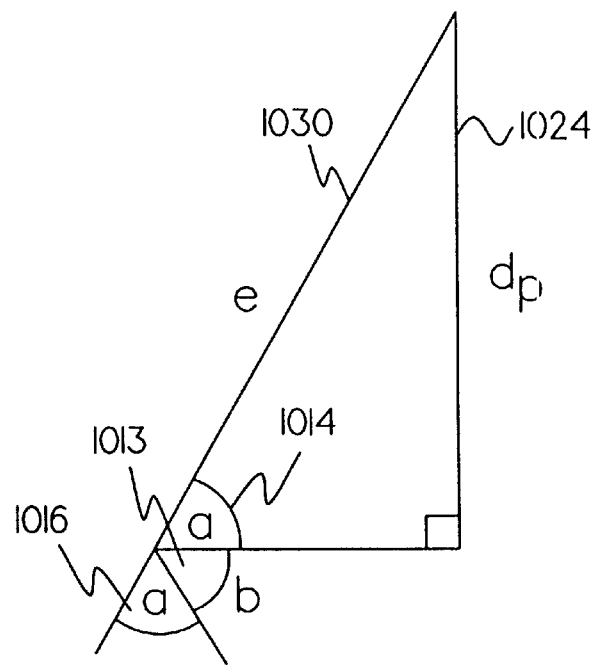

Now using FIG. 11F, which shows an illustration of the reduced relationship between the distance e 1030, $d_p$ 1024, angle a 1014 and angle b 1013, an equation to solve for the position c 1002 of the part 1000 in the z-dimension is derived as follows:

$$\frac{e}{\sin 90°} = \frac{dp}{\sin\theta} = \frac{dp}{\sin\left(45° + \frac{\theta}{2}\right)} = \frac{e}{1}$$

$$e = \frac{dp}{\sin\left(45° + \frac{\theta}{2}\right)}$$

$$\frac{ds}{\sin(90°-D)} = \frac{dp}{\sin\left(45° + \frac{\theta}{2}\right)}$$

$$dp = \frac{ds \sin(45° + \theta/2)}{\sin(90°-D)}$$

$$t = dp - S$$

$$c \sin(90° - \theta) = dp - S$$

$$c \sin(90° - \theta) = \frac{ds \sin(45° + \theta/2)}{\sin(90°-D)} - d_B \sin\theta$$

$$90° - D = 90° - (45° - \theta/2) = 45° + \theta/2$$

$$C = \frac{\frac{ds \sin(45° + \theta/2)}{\sin(45° + \theta/2)} - d_B \sin\theta}{\sin(90°-\theta)} = \frac{ds - d_B \sin\theta}{\sin(90°-\theta)}$$

$$\sin(90° - \theta) = \cos\theta \quad c = \frac{ds - d_B \sin\theta}{\cos\theta} = \frac{ds}{\cos\theta} - \frac{d_B \sin\theta}{\cos\theta}$$

$$C = \frac{ds}{\cos\theta} - d_B \tan\theta$$

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An apparatus for three dimensional inspection of electronic leads, the apparatus comprising:
    a) a transparent reticle having a top surface, wherein the transparent reticle receives a part having electronic leads for inspection on a central portion of the top surface;
    b) a fixed optical element attached to the top surface of the transparent reticle, wherein the fixed optical element is positioned to reflect a side view of the part through the transparent reticle;
    c) a camera located below the transparent reticle positioned to receive an image, including a bottom view of the part through the transparent reticle and a side view of the part from the fixed optical element, wherein the camera has an image data output representative of the bottom view and the side view;
    d) a reference line located on the transparent reticle, wherein the reference line is positioned to provide a view to the camera of the reference line between the bottom view and the side view; and
    e) a processor connected to receive the image data output, wherein the processor performs a three dimensional analysis on the image data output to inspect the electronic leads, wherein the processor has an electronic lead inspection result.

2. The apparatus of claim 1 wherein the apparatus employs a reticle mask for calibration, wherein the reticle mask further comprises a calibration dot pattern.

3. The apparatus of claim 1 further comprising four fixed optical elements attached around the central portion of the transparent reticle to provide four side views of the part to the camera.

4. The apparatus of claim 1 wherein the fixed optical element further comprises a prism.

5. The apparatus of claim 1 wherein the fixed optical element further comprises a mirror.

6. The apparatus of claim 1 wherein the image data from the camera is stored in a memory.

7. The apparatus of claim 1 wherein the processor determines a height above the transparent reticle of an object according to the following equation:

$$Z = D_S \tan(45° - \theta/2) - (D_B - D_S) \tan\theta$$

where:
   $D_S$ = distance from a reference edge to the side view image of the object;
   $D_B$ = distance from a reference edge to the bottom view image of the object;
   $\theta$ = angle formed by a ray emanating from the object reflected by the fixed optical element and received by the camera and a plane intersecting the object parallel to the transparent reticle plane; and
   Z = distance along the Z axis from the transparent reticle plane to the object.

8. The apparatus of claim 7 wherein an intersection of a reflective face of the fixed optical element and the transparent reticle is the reference edge.

9. The apparatus of claim 1 wherein the processor determines a height above the transparent reticle of an object according to the following equation:

$$Z = (d_S + R) \tan(45° - \theta/2) - (d_B - d_S) \tan\theta$$

where:

$d_S$=distance from a reference edge to the side view image of the object;

$d_B$=distance from a reference edge to the bottom view image of the object;

θ=angle formed by a ray emanating from the object reflected by the fixed optical element and received by the camera and a plane intersecting the object parallel to the transparent reticle plane;

R=offset of reference line and the intersection between a reflective face of the fixed optical element and the transparent reticle; and Z=distance along the Z axis from the transparent reticle plane to the object.

10. The apparatus of claim 9 wherein the processor determines θ and an offset R according to the following equations:

$$\theta = \text{ARCTAN}\left(\frac{\Delta Z}{\Delta X}\right)$$

$$R = \frac{(d_B - d_s)\tan\theta}{\tan(45° - \theta/2)} - d_s$$

where

Δx=distance between two objects on the bottom view; and

Δz=corresponding distance between the two objects on the side view.

11. The apparatus of claim 1 wherein the camera is adjusted to provide a depth of focus encompassing an optical path from the part to the camera and an optical path from the part to the fixed optical element to the camera.

12. The apparatus of claim 1 wherein a vacuum holder suspends the part above the transparent reticle holder.

13. The apparatus of claim 12 wherein the central portion of the transparent reticle is cut out.

14. The apparatus of claim 1 further comprising a pedestal mounted on the central portion of the transparent reticle to receive the part.

15. The apparatus of claim 1 wherein the camera is positioned so that the axis of the camera is substantially perpendicular to a surface of the transparent reticle.

16. The apparatus of claim 1 wherein the processor determines a height above the transparent reticle of an object according to the following equation:

$$C = \frac{d_S}{\cos\theta} - d_B \tan\theta$$

where:

$d_S$=distance from a reference edge to the side view image of the object;

$d_B$=distance from a reference edge to the bottom view image of the object;

θ=angle formed by a ray emanating from the object reflected by the fixed optical element and received by the camera and a plane intersecting the object parallel to the transparent reticle plane; and C=distance along the Z axis from the transparent reticle plane to the object.

17. The apparatus of claim 16 wherein the reference edge is located on the transparent reticle plane.

18. A method for three dimensional inspection of electronic leads from a single image, the method comprising the steps of:

a) providing a transparent reticle having a top surface;

b) placing a part having electronic leads for inspection on a central portion of the top surface of the transparent reticle;

c) providing fixed optical elements for providing a side perspective of the part;

d) providing a camera located beneath the transparent reticle to receive an image of the part and the side perspective provided by the fixed optical elements wherein the camera provides image data;

e) providing a reference line located on the transparent reticle, wherein the reference line is positioned to provide a view to the camera of the reference line between the bottom view and the side view; and f) processing the image data with a computer to provide a three dimensional analysis of the part.

19. The method of claim 18 further comprising the step of calibrating the computer using a reticle mask.

20. The method of claim 19 wherein calibrating the computer further comprises calibration of a bottom view by:

a) locating calibration dots on the reticle mask visible directly from the bottom view;

b) determining a location and size of each dot;

c) storing a location and size of each dot in memory;

d) determining state values for calibration of the bottom view by comparing the location and size of each dot with known values; and e) storing the state values in memory.

21. The method of claim 20 wherein calibrating the computer further comprises calibration of a side view by:

a) locating the calibration dots visible in each of the fixed optical elements;

b) locating a reference edge;

c) calculating a distance from the reference edge to each dot in the side view image and the bottom view image;

d) determining state values for the fixed optical elements from known values; and e) storing the state values in memory.

22. A method for providing three dimensional inspection of an object having electronic leads from a single image, the method comprising the steps of:

a) waiting for an inspection signal;

b) acquiring an image of the object including a bottom view and a side view;

c) processing the image to find a reference line located on the transparent reticle, wherein the reference line is positioned to provide a view to the camera of the reference line between the bottom view and the side view, a rotation, x placement and y placement of the object;

d) locating the electronic leads of the object in the bottom view;

e) locating the electronic leads of the object in the side view;

f) determining a reference point for each lead;

g) converting pixel values to world values;

h) converting world values to part values;

i) converting part values to measurement values, wherein the measurement values are determined by comparing the part values to predetermined part values; and j) providing a part result based on the measurement values and predetermined tolerance values.

23. The method of claim 22 wherein the part result comprises a result selected from the group of: a pass result, a fail result and a rework result.

24. The method of claim 22 wherein the predetermined tolerance values further comprise pass tolerance values and fail tolerance values.

25. The method of claim 24 wherein the part result comprises a pass result if the measurement values are less than or equal to the pass tolerance values, a fail result if the measurement values exceed the fail tolerance values and a rework result otherwise.

26. The method of claim 22 wherein the image is stored in memory.

27. The method of claim 22 wherein the object is removed after the image is acquired and a next object placed while the part result is calculated.

28. The method of claim 22 wherein the steps of locating the electronic leads of the object in the bottom view and locating the electronic leads of the object in the side view further comprises the steps of:
   a) processing an image of a lead wherein the image comprises an image of a lead tip to generally locate a region of the image that contains the lead tip;
   b) defining a region of interest that contains the lead tip including a lead tip edge and lead tip sides;
   c) performing a subpixel edge detection over the region of interest to find a location of a center of the lead tip.

29. The method of claim 28 wherein the region of interest is sized to include only an image of one full lead.

30. An apparatus for three dimensional inspection of electronic leads, the apparatus comprising:
   a) a light source;
   b) a transparent reticle having a top surface, wherein the transparent reticle receives a part having electronic leads for inspection on a central portion of the top surface;
   c) a light diffuser positioned above the transparent reticle, wherein the light diffuser receives illumination from the light source and provides diffused illumination;
   d) a fixed optical element attached to the top surface of the transparent reticle, wherein the fixed optical element is positioned to reflect a side view of the part through the transparent reticle;
   e) a camera located below the transparent reticle positioned to receive an image, including a bottom view of the part through the transparent reticle and a side view of the part from the fixed optical element, wherein the camera has an image data output representative of the bottom view and the side view; and
   f) a processor connected to receive the image data output, wherein the processor performs a three dimensional analysis on the image data output to inspect the electronic leads, wherein the processor has an electronic lead inspection result.

31. The apparatus of claim 30 wherein the light diffuser is fixed above the reticle.

32. The apparatus of claim 30 wherein the light diffuser is attached to a part holder.

33. The apparatus of claim 30 wherein the light source comprises a plurality of light arrays positioned around the transparent reticle.

* * * * *